(12) United States Patent
Kane

(10) Patent No.: US 10,321,714 B1
(45) Date of Patent: Jun. 18, 2019

(54) WATER COOLED VAPORIZING SYSTEM

(71) Applicant: Randy M. Kane, Clearwater, FL (US)

(72) Inventor: Randy M. Kane, Clearwater, FL (US)

(*) Notice: Subject to any disclaimer, the term of this patent is extended or adjusted under 35 U.S.C. 154(b) by 1 day.

(21) Appl. No.: 15/131,973

(22) Filed: Apr. 18, 2016

(51) Int. Cl.
| | |
|---|---|
| *A24F 47/00* | (2006.01) |
| *A24F 1/30* | (2006.01) |
| *A61M 11/04* | (2006.01) |
| *A61M 15/00* | (2006.01) |
| *H02J 7/00* | (2006.01) |

(52) U.S. Cl.
CPC ............. *A24F 47/008* (2013.01); *A24F 1/30* (2013.01); *A61M 11/042* (2014.02); *A61M 15/0021* (2014.02); *H02J 7/0052* (2013.01); *H02J 2007/0062* (2013.01)

(58) Field of Classification Search
CPC .. A24F 47/008; A24F 1/02; A24F 1/16; A24F 1/30
USPC ................. 131/173, 198, 200, 331
See application file for complete search history.

(56) References Cited

U.S. PATENT DOCUMENTS

| | | | | |
|---|---|---|---|---|
| 2,815,030 | A * | 12/1957 | Wenger ..................... | A24F 1/30 131/173 |
| 3,394,710 | A * | 7/1968 | Ping-Chuan .............. | A24F 1/30 131/173 |
| 3,804,100 | A * | 4/1974 | Fariello ..................... | A24F 3/00 131/173 |
| 4,133,318 | A * | 1/1979 | Gross ........................ | A24F 1/30 131/173 |
| 4,203,455 | A * | 5/1980 | Byrd, Jr. ................... | A24F 1/30 131/173 |
| 5,738,116 | A * | 4/1998 | Truelove ................... | A24F 1/30 131/173 |
| 6,453,908 | B1 * | 9/2002 | Caballero ................. | A24F 1/30 131/173 |
| 8,534,296 | B2 * | 9/2013 | Groff ........................ | A24F 1/30 131/200 |
| 2007/0068523 | A1 * | 3/2007 | Fishman ........... | A61M 16/0051 128/203.12 |
| 2008/0029107 | A1 * | 2/2008 | Ruff ......................... | A24F 1/30 131/173 |

(Continued)

OTHER PUBLICATIONS

RealCigReview. "Zobo Cigarette Water Filter from Red Mana." YouTube, YouTube, May 10, 2013, www.youtube.com/watch?v=UdefJSf5fF8. (Year: 2013).*

*Primary Examiner* — Seyed Masoud Malekzadeh
*Assistant Examiner* — Taryn Trace Willett

(57) ABSTRACT

A housing assembly is formed of upper and lower cases with top and bottom plates and an intermediate plate separating the upper and lower cases. An agitation assembly includes water in the lower case. A plurality of paddles submerged in the water are rotatable to agitate the water. An inlet assembly includes an inlet pipe having a top end above the top plate and a bottom end submerged in the water. A heating assembly includes a chamber interiorly and a cylinder exteriorly forming an annular passageway terminating at the top end of the inlet pipe. A heating coil system within the vaporizing chamber is adapted to vaporize the selected material whereby vapors released will tumble down the annular passageway then down the inlet pipe into the water. An outlet assembly includes an outlet pipe having a top end and a bottom end terminating below above the water.

1 Claim, 4 Drawing Sheets

(56) References Cited

U.S. PATENT DOCUMENTS

| | | | |
|---|---|---|---|
| 2012/0097660 A1* | 4/2012 | Bao | A61M 11/041 219/209 |
| 2012/0199572 A1* | 8/2012 | Shen | A61M 11/041 219/438 |
| 2015/0040926 A1* | 2/2015 | Saydar | A61M 15/00 131/329 |
| 2015/0122275 A1* | 5/2015 | Wu | A24F 1/30 131/329 |
| 2015/0136155 A1* | 5/2015 | Verleur | A24F 47/008 131/328 |
| 2015/0257443 A1* | 9/2015 | Rado | A24F 47/00 392/390 |
| 2016/0219937 A1* | 8/2016 | Rado | A24F 47/008 |
| 2016/0227838 A1* | 8/2016 | Johnson | H04R 1/028 |
| 2016/0278436 A1* | 9/2016 | Verleur | A24F 47/008 |
| 2016/0295911 A1* | 10/2016 | Kalousek | A24F 1/30 |
| 2016/0353800 A1* | 12/2016 | Di Carlo | A24F 47/008 |
| 2017/0055579 A1* | 3/2017 | Kuna | A24F 47/008 |
| 2017/0143035 A1* | 5/2017 | Pucci | A24F 1/30 |
| 2017/0224013 A1* | 8/2017 | Huang | A24F 47/008 |

* cited by examiner

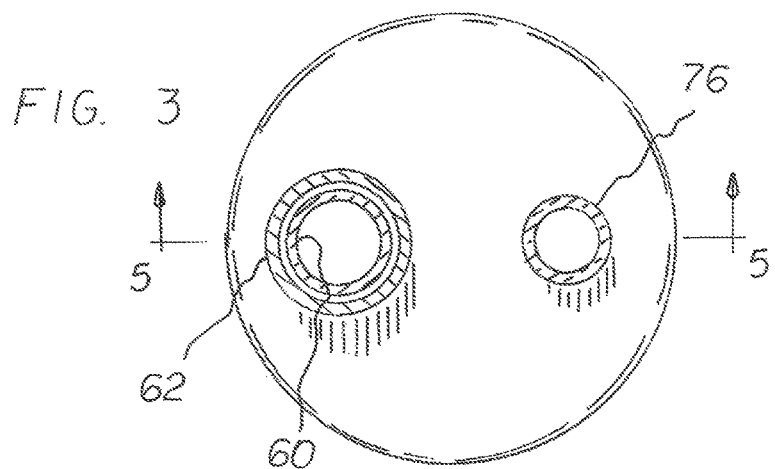
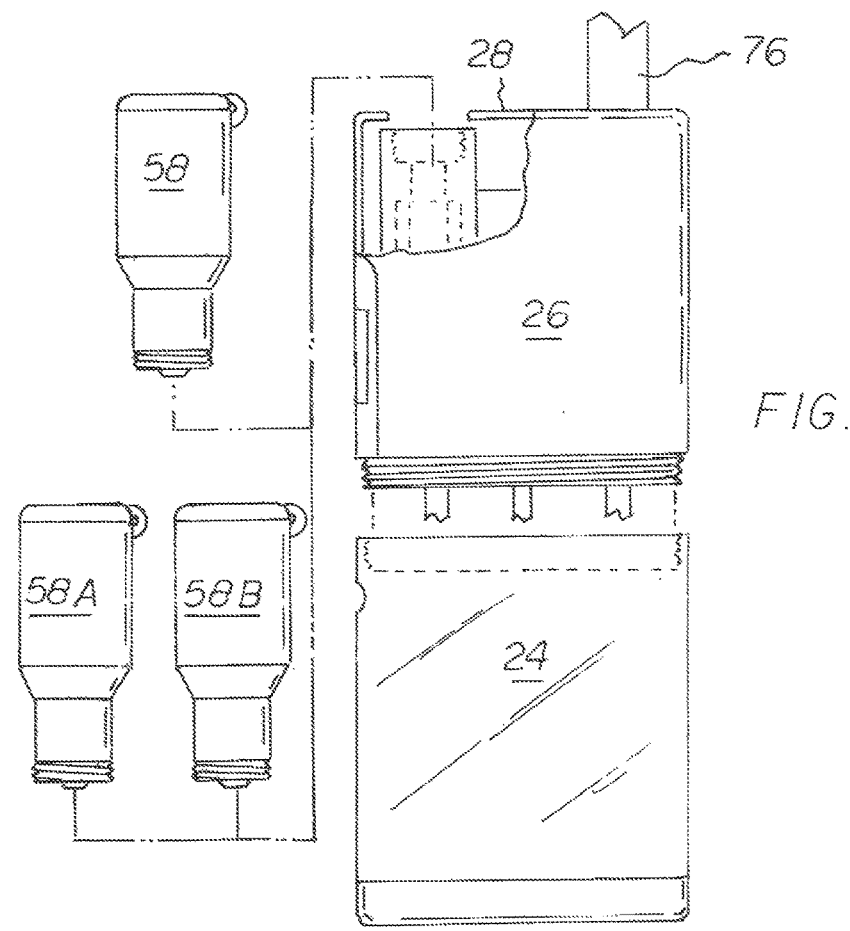

WATER COOLED VAPORIZING SYSTEM

BACKGROUND OF THE INVENTION

Field of the Invention

The present invention relates to a 3 in 1 water cooled vaporizing system which, allows for a single unit to vaporize herbs, oils, liquids, and concentrates, including tobacco or medicinal marijuana, the vaporizing being done in an improved, safer, more versatile hookah, water pipe style. The system is a smokeless system that heats up the herbal material Instead of combustion, the vaporizing process utilizes a conduction method for the purpose of creating inhalable vapors which cause the essential oils, which contain the active ingredients of the herbal material, to boil until it creates a cooled vapor that can be safely inhaled.

The purpose of this invention is to allow for the user to select a material to be vaporized and place it in 1 of 3 specifically newly created conduction vaporizing chambers that allows for the vaporized material to be drawn downward into the water reservoir where spinning paddles agitate and percolate the water in the reservoir to cleanse, cool and increase the flavor of the cooled vapor inhaled by the user.

Regarding functionality, the selected material like herbals, oils, concentrates, and liquids, including tobacco or medical marijuana is placed in the inventor's newly created vaporizing chamber which is then attached to the upper housing cylinder where electronic sensors detect the chamber attached and heats the chamber to the recommended temperature shown on a liquid crystal display screen attached to the chamber. Once the designated temperature is reached a light emitting diode light is illuminated, which advises the user the desired temperature has been reached. A button is pushed to activate the convection process and the spinning of the paddles in the water reservoirs. The user then inhales through the mouth piece, which draws the heated vapor down from the vaporizing chamber, through the housing into the water reservoir where it is cooled, cleansed, flavor-enhanced and then inhaled as a cooled vapor in a safe, medically-acceptable+, convenient, and economical manner.

Description of the Prior Art

The use of vaporizing systems of known designs and configurations is known in the prior art. More specifically, vaporizing systems of known designs and configurations previously devised and utilized for the purpose of creating inhalable vapors are known to consist basically of familiar, expected, and obvious structural configurations, notwithstanding the myriad of designs encompassed by the crowded prior art which has been developed for the fulfillment of countless objectives and requirements.

While these known devices fulfill their respective, particular objectives and requirements, including tobacco and medical marijuana, they do not describe a vaporizing system that allows for the selective vaporizing of herbs, oils, liquids and concentrates to a heated vapor, and for agitating a quantity of water below, and for passing the vaporized material as heated vapor through the water to cleanse and cool an enhance the flavor and create an inhalable cooled vapor. The heating, agitating, and passing are all done in a safe, medically-acceptable+, convenient, and economical manner.

In this respect, the water cooled vaporizing 3 in 1 system according to the present invention substantially departs from the conventional concepts and designs of the prior art, and in doing so provides an apparatus primarily developed for the purpose of selective heating of vaporizing material to a heated vapor above, and for spinning, percolating and agitating a quantity of water below, and for passing the vaporized material as heated vapors through the water to cool, cleanse and enhance the flavor and create inhalable cooled vapor, the heating and the agitating and the passing all being done in a safe, medically-acceptable+, convenient, and economical manner. Therefore, it can be appreciated that there exists a continuing need for a new and improved water cooled vaporizing 3 in 1 system which can be used for selectively heating vaporizing material to a heated vapor above, for agitating a quantity of water below, and for passing the heated vapor through the water to create an inhalable cooled vapor. The heating, agitating, and passing are all done in a safe, medically-acceptable+, convenient, and economical manner. In this regard, the present invention substantially fulfills this need.

SUMMARY OF THE INVENTION

In view of the disadvantages inherent in the known types of vaporizing systems of known designs and configurations now present in the prior art, the present invention provides an improved water cooled vaporizing 3 in 1 system. As such, the general purpose of the present invention, which will be described subsequently in greater detail, is to provide a new and improved water cooled vaporizing 3 in 1 system and method which has all the advantages of the prior art and none of the disadvantages.

To attain this, for a broad perspective, the present invention essentially comprises a housing assembly formed of upper and lower cases with top and bottom plates and an intermediate plate separating the upper and lower cases. An agitation assembly includes water in the lower case. A plurality of paddles submerged in the water are rotatable to agitate the water. An inlet assembly includes an inlet pipe having a top end above the top plate and a bottom end submerged in the water. A heating assembly includes a chamber interiorly and a cylinder exteriorly forming an annular passageway terminating at the top end of the inlet pipe. A heating coil system within the vaporizing chamber is adapted to vaporize the selected material whereby vapors released will tumble down the annular passageway then down the inlet pipe into the water. An outlet assembly includes an, outlet pipe having a top end and a bottom end terminating below above the water.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved vaporizing system which has all of the advantages of the prior art vaporizing systems of known designs and configurations and none of the disadvantages.

It is another object of the present invention to provide a new and improved vaporizing system which may be easily and efficiently manufactured and marketed.

It is a further object of the present invention to provide a new and improved vaporizing system which is of durable and reliable constructions.

An even further object of the present invention is to provide a new and improved vaporizing system which is susceptible of a low cost of manufacture with regard to both materials and labor, and which accordingly is then susceptible of low prices of sale to the consuming public, thereby making such vaporizing system economically available to the buying public.

Lastly, it is an object of the present invention to provide a vaporizing system for selective heating of vaporizing material to a heated vapor above, and for spinning, percolating and agitating a quantity of water below, and for passing the vaporized material as heated vapors through the water to cool, cleanse and enhance the flavor and create inhalable cooled vapor, the heating and the agitating and the passing all being done in a safe, medically-acceptable+, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross sectional view taken along line 3-3 of FIG. 1.

FIG. 4 is an exploded front elevational view of the system of the prior Figures.

The same reference numerals refer to the same parts throughout the various Figures.

DESCRIPTION OF THE PREFERRED EMBODIMENT

Figures 1, 2:
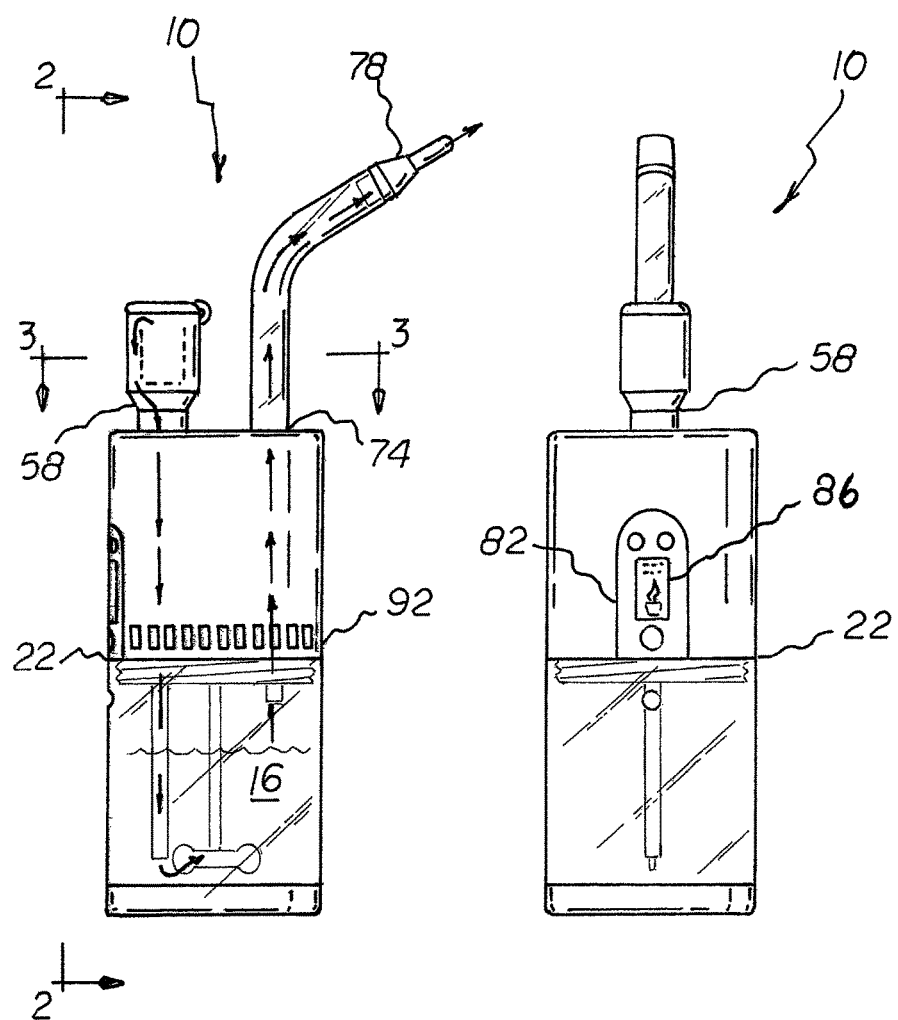
FIG. 1 is a front elevational view of a vaporizing system constructed in accordance with the principles of the present invention.
FIG. 2 is a side elevational view taken along line 2-2 of FIG. 1.
Figures 5, 6:
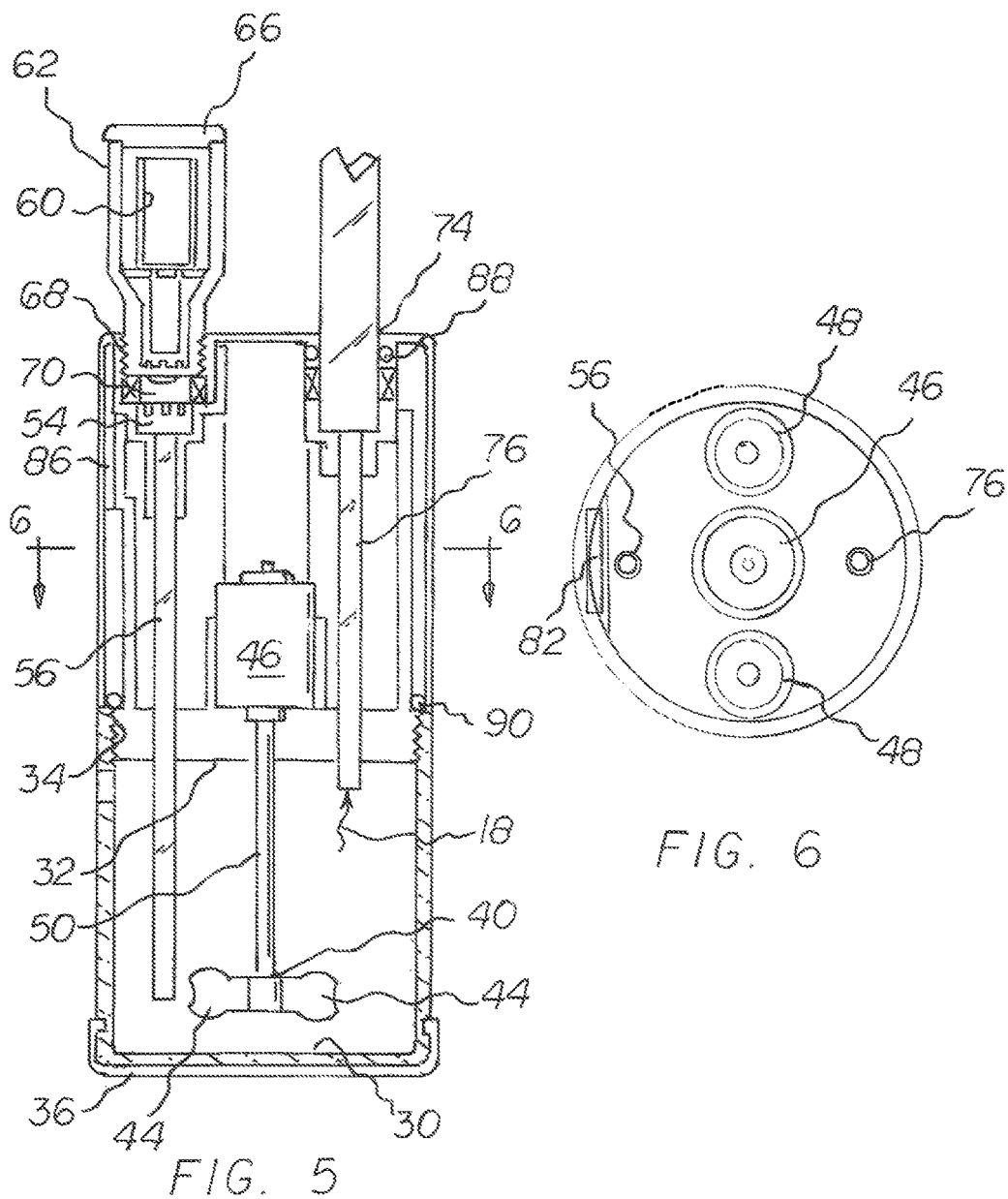
FIG. 5 is a cross sectional view taken along line 5-5 of FIG. 3.
FIG. 6 is a cross sectional view taken along line 6-6 of FIG. 5.
Figure 7:
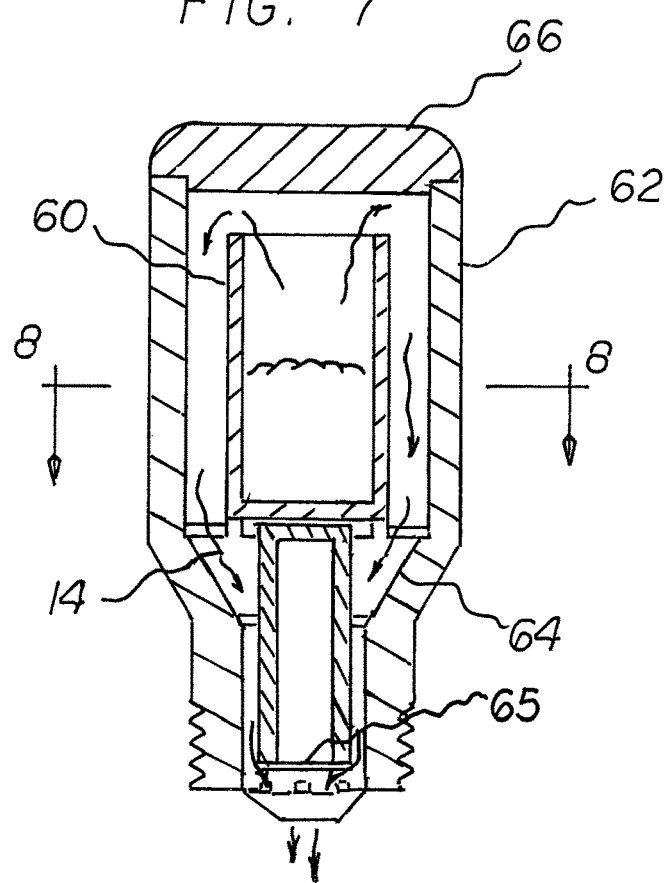
FIG. 7 is an enlarged cross sectional view of the heating assembly shown in FIG. 1.
Figure 8:
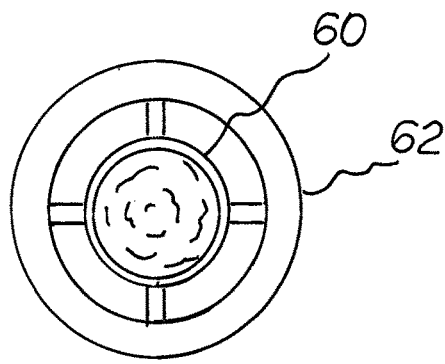
FIG. 8 is a cross sectional view taken along line 8-8 of FIG. 7.

With reference now to the drawings, and in particular to FIG. 1 thereof, the preferred embodiment of the new and improved water cooled vaporizing system embodying the principles and concepts of the present invention and generally designated by the reference numeral 10 will be described.

The present invention, the vaporizing system 10 is comprised of a plurality of components. Such components in their broadest context include a housing assembly, an agitation assembly, and an inlet assembly, a heating assembly, and an outlet assembly. Such components are individually configured and correlated with respect to each other so as to attain the desired objective.

From a specific perspective, the invention of the present application is a vaporizing system for selective heating of herbal material 12 to a heated vapor 14, for agitating and percolating a quantity of water 16, and for passing vaporized material through the water to create an inhalable cooled vapor 18. The heating, the agitating, and the passing all being done in a safe, medically-acceptable, convenient, and economical manner.

A housing assembly 22 is provided. The housing assembly has a cylindrical, configuration with a height and with a diameter. The height is between 200 percent and 250 percent of the diameter. The housing assembly is formed of a lower case 24 with a lower height and an upper case 26 with an upper height. The lower case is fabricated of a transparent medical glass. The upper case is fabricated of an opaque PVC or stainless steel material. The upper height is between 90 percent and 110 percent of the lower height. The housing assembly has a rigid top plate 28, a rigid bottom plate 30, and a rigid intermediate plate 32. The rigid intermediate plate is coupled to the upper case separating the upper case and the lower case during use. Screw threads 34 couple the upper case and the lower case. An anti-skid pad 36 is coupled to the lower case from below to prevent slipping.

An agitation/peculation assembly 40 is next provided in the housing assembly. The agitation assembly includes the quantity of water 16 in the lower case. A plurality of paddles 44 are submerged in the quantity of water. A motor 46 with 2 lithium batteries 48 to power the motor is provided in the upper case. A drive shaft 50 couples the motor and the plurality of paddles whereby powering the motor will rotate the drive shaft and rotate the paddles and thereby spin & agitate the quantity of water.

Next provided is an inlet assembly 54. The inlet assembly includes an inlet pipe 56. The inlet pipe has a top end above the top plate. The inlet pipe has a bottom end terminating below the intermediate plate submerged in the quantity of water. The inlet pipe includes an intermediate extent passing through the top plate and the upper case and the intermediate plate.

A heating assembly 58 is next provided. The heating assembly has a 3 individual vaporizing chambers 58, 58A, 58B to handle herbal, oils and or concentrates of selected material 60 interiorly and a stainless steel cylinder 63 exteriorly. A coupling section 64 extends downwardly from the stainless steel or glass cylinder forming an annular passageway between the vaporizing chamber and the stainless steel or glass cylinder with a lid 66 there above. The annular passageway terminates at the top end of the inlet pipe. Upper screw threads 68 removably couple the heating assembly to the upper case. A plurality of heating coils & assemblies are selectable to conduct the material within the vaporizing chamber as a function of the nature of the vaporized material in the vaporizing chamber. The vaporized material 12 in the vaporizing chamber is chosen from the class of materials consisting of herbs, concentrates, and liquids. A heater 70 adjacent to the vaporizing chamber is adapted to heat the vaporizing material through convection. In this manner, the vapors created from the convected material will tumble down the annular passageway, then down the inlet pipe into the quantity of water.

An outlet assembly 74 is next provided. The outlet assembly includes an outlet pipe 76. The outlet pipe has a top end above the top plate. The outlet pipe includes a bottom end terminating below the intermediate plate above the quantity of water. The outlet pipe includes an intermediate extent passing through the top plate and the upper case and the bottom plate. The outlet pipe has a lower extent with a smaller diameter and an upper extent with a larger diameter. A mouthpiece 78 is coupled to the top end of the outlet pipe. The mouthpiece is adapted to be drawn on by the user to inhale the vapors passed through the quantity of water agitated in the lower case.

Lastly, a control assembly 82 is provided. The control assembly includes operator accessible components. From top to bottom laterally spaced temperature buttons are provided to select higher and lower temperatures for the heater should the user prefer to vaporize at a temperature not preset to the designated chamber attached. A display of a preset temperature is variable by pressing the laterally spaced buttons. A heating signal is provided to indicate, when illuminated, that the heater is approaching a preset temperature. A power signal is provided to indicate, when illuminated, that power is on. A power/heater button is provided to be depressed to turn the power on and off.

The three vaporizing chambers 58, 58A, and 58B allow for the user to select a material to be vaporized and place it in 1 of the 3 specifically newly created conduction vaporizing chambers. The control assembly is designed to recognize the specific chamber screwed into the housing assembly and then heat the elements within that chamber to the preset temperatures designated for the material including herbs, oils, liquids, concentrates to be vaporized.

The control assembly also includes a) a printed circuit board 86 in the upper case, b) an upper light emitting diode strip 88 in the lid adjacent to the outlet pipe, c) lower light emitting diode strip 90 in the upper case adjacent to the lower screw threads, and d) a USB port 92 is provided for charging the system.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A vaporizing system for selective heating of vaporizing material (12) to a heated vapor (14) above, and for spinning, percolating and agitating a quantity of water (16) below, and for passing the vaporized material as heated vapors through the water to cool, cleanse and enhance the flavor and create inhalable cooled vapor (18), the system comprising, in combination:

a housing assembly (22) having a cylindrical configuration with a height and with a diameter, the height being between 200 percent and 250 percent of the diameter, the housing assembly formed of a lower case (24) with a lower height, the housing assembly formed of an upper case (26) with an upper height, the lower case being fabricated of a transparent medical glass, the upper case being fabricated of an opaque stainless steel material, the upper height being between 90 percent and 110 percent of the lower height, the housing assembly having a rigid top plate (28), and a rigid bottom plate (30), and a rigid intermediate plate (32) coupled to the upper case separating the upper case and the lower case during use, screw threads (34) separably coupling the upper case and the lower case, an anti-skid pad (36) coupled to the lower case from below;

an agitation assembly (40) in the housing assembly, the agitation assembly including a reservoir with the quantity of water (16) in the lower case, a plurality of paddles (44) submerged in the quantity of water, a motor (46) with a lithium battery (48) in the upper case to power the motor, a drive shaft (50) coupling the motor and the plurality of paddles whereby powering the motor will rotate the drive shaft and rotate the paddles and thereby agitate the quantity of water;

an inlet assembly (54) including an inlet pipe (56) having a top end located above the top plate, the inlet pipe having a bottom end terminating below the intermediate plate submerged in the quantity of water, the inlet pipe including an intermediate extent passing through the top plate and the upper case and the intermediate plate;

a designated heating assembly selected from the class including a plurality of heating assemblies, each of the plurality of heating assemblies having a corresponding vaporizing chamber (60) interiorly and a stainless steel cylinder (62) exteriorly, a coupling section (64) extending downwardly from the stainless steel cylinder forming an annular passageway between the vaporizing chamber and the stainless steel cylinder with a lid (66) there above, the annular passageway terminating at the top end of the inlet pipe, an upper coupler (68) removably coupling the heating assembly to the upper case, each corresponding vaporizing chamber having a plurality of heating coils (65) selectable to heat the vaporizing material in the vaporizing chamber as a function of the nature of the vaporizing material in the vaporizing chamber, the vaporizing material (12) in the vaporizing chamber being chosen from the class of vaporizing materials consisting of herbs, concentrates, and liquids, each of the heating assemblies further incorporating a heater (70) adjacent to the corresponding vaporizing chamber adapted to heat the vaporizing material through convection whereby gaseous output of the heated vaporizing material will tumble down the annular passageway then down the inlet pipe into the quantity of water;

an outlet assembly (74) including an outlet pipe (76) having a top end located above the top plate, the outlet pipe including a bottom end terminating below the intermediate plate in, the quantity of water, the outlet pipe including an intermediate extent passing through the top plate and the upper case and the bottom plate, the outlet pipe having a lower extent with a smaller diameter and an upper extent with a larger diameter, a mouthpiece (78) coupled to the top end of the outlet pipe adapted to be sucked by a user to draw up inhalable cooled vapor passed through the quantity of water agitated in the lower case; and a control assembly (82) being configured to recognize the designated heating assembly selected from the plurality of heating assemblies that is integrated in the upper case via the coupling section, the control assembly further configured to control the heating coils of the corresponding vaporizing chamber of the designated heating assembly according to a preset temperature according to the selected vaporizing material for which the designated heating assembly and the corresponding vaporizing chamber is configured, the control assembly further including a plurality of spaced operator accessible components, the operator accessible components including from top to bottom laterally spaced temperature buttons to select higher and lower temperatures for the heater, a display of a preset temperature variable by pressing the laterally spaced buttons, a heating signal to indicate when illuminated that the heater is approaching a present temperature, a power signal to indicate when illuminated that power is on, a power/heater button to be depressed to turn the power on and off, a printed circuit board (86) in the upper case, an upper light emitting diode strip (88) in the lid adjacent to the outlet pipe, a lower light emitting diode strip (90) in the upper case adjacent to the lower screw threads, and a USB port (92) for charging the system.

\* \* \* \* \*